(12) United States Patent
Akinwande et al.

(10) Patent No.: US 11,452,441 B2
(45) Date of Patent: Sep. 27, 2022

(54) SYSTEM AND METHOD FOR TRAINING A LAZY EYE

(71) Applicant: International Business Machines Corporation, Armonk, NY (US)

(72) Inventors: Victor Abayomi Akinwande, Nairobi (KE); Charles Muchiri Wachira, Karatina (KE); William Ogallo, Nairobi (KE); Aisha Walcott, Nairobi (KE)

(73) Assignee: International Business Machines Corporation, Armonk, NY (US)

( * ) Notice: Subject to any disclaimer, the term of this patent is extended or adjusted under 35 U.S.C. 154(b) by 454 days.

(21) Appl. No.: 16/727,892

(22) Filed: Dec. 26, 2019

(65) Prior Publication Data

US 2021/0196115 A1   Jul. 1, 2021

(51) Int. Cl.
*A61B 3/08*   (2006.01)
*A61B 3/113*   (2006.01)
*G06F 3/01*   (2006.01)
*A61H 5/00*   (2006.01)

(52) U.S. Cl.
CPC .............. *A61B 3/085* (2013.01); *A61B 3/113* (2013.01); *A61H 5/00* (2013.01); *G06F 3/012* (2013.01); *G06F 3/013* (2013.01)

(58) Field of Classification Search
CPC ........... A61B 3/085; A61B 3/113; A61H 5/00; G06F 3/012; G06F 3/013
See application file for complete search history.

(56) References Cited

U.S. PATENT DOCUMENTS

| | | | |
|---|---|---|---|
| 7,033,026 B2 | 4/2006 | Spector | |
| 8,820,930 B2 * | 9/2014 | Fateh | A61B 3/022 351/205 |
| 2004/0080706 A1 | 4/2004 | Howard | |
| 2010/0092049 A1 | 4/2010 | Schroeder et al. | |
| 2016/0270656 A1 * | 9/2016 | Samec | A61B 5/369 |
| 2017/0285743 A1 | 10/2017 | Yu et al. | |
| 2019/0046029 A1 | 2/2019 | Tomasi et al. | |

FOREIGN PATENT DOCUMENTS

WO   WO2013131526 A1   9/2013

OTHER PUBLICATIONS

McGill University Health Centre. "Lazy eye disorder treated with video game Tetris." ScienceDaily. ScienceDaily, Apr. 22, 2013, www.sciencedaily.com/releases/2013/04/130422122953.htm.
Helen Knight, Picower Institute for Learning and Memory, Creating new treatments for amblyopia, Nov. 21, 2016, MIT News, 3 Pages, downloaded from http://news.mit.edu/2016/creating-new-treatments-for-amblyopia-1121.

(Continued)

*Primary Examiner* — Simon King
(74) *Attorney, Agent, or Firm* — Shimon Benjamin; Otterstedt & Kammer PLLC (57) ABSTRACT

A comfortability-tension threshold for a user is determined and a current pose of the user and a determined optimal pose are compared. The current pose and the determined optimal pose are mapped to an angle for adjusting on-screen content of a display of the computer system and the on-screen content of the display of the computer system is adjusted based on the angle.

20 Claims, 8 Drawing Sheets

(56) References Cited

OTHER PUBLICATIONS

Žiak et al. Amblyopia treatment of adults with dichoptic training using the virtual reality oculus rift head mounted display: preliminary results, BMC Ophthalmology (2017) 17:105 DOI 10.1186/s12886-017-0501-8 http://news.mit.edu/2016/creating-new-treatments-for-amblyopia-1121.

Pfister et al., Recognising Spontaneous Facial Micro-expressions, 2011 IEEE International Conference on Computer Vision, pp. 1449-1456.

* cited by examiner

SYSTEM AND METHOD FOR TRAINING A LAZY EYE

BACKGROUND

The present invention relates to the electrical, electronic and computer arts, and more specifically, to artificial intelligence (AI), machine learning, and machine reasoning.

Amblyopia, also known as lazy eye, is a vision development disorder, often beginning in childhood, where one eye fails to achieve normal visual acuity and, as a consequence, the brain favors the other eye. An estimated 3% of Americans are said to be Amblyopic. It is often treated by wearing an eye patch to force usage of the lazy eye or other visual training. The greater chances of success occur when treatment is done at an early age. Other options include surgery or atropine, an eye drop for the stronger eye that temporarily weakens it, forcing the usage of the lazy eye. Current ways to treat a lazy eye require active compliance and, due to often poor compliance and variable outcomes, their effects are often minimal.

SUMMARY

Principles of the invention provide techniques for training a lazy eye. In one aspect, an exemplary method for training a lazy eye with a computer system includes the operations of determining a comfortability-tension threshold for a user; comparing a current pose of the user and a determined optimal pose; mapping the current pose and the determined optimal pose to an angle for adjusting on-screen content of a display of the computer system; and adjusting the on-screen content of the display of the computer system based on the angle.

In one aspect, an apparatus comprises a memory; a display; and at least one processor, coupled to said memory and said display, and operative to perform operations comprising determining a comfortability-tension threshold for a user; comparing a current pose of the user and a determined optimal pose; mapping the current pose and the determined optimal pose to an angle for adjusting on-screen content of the display; and adjusting the on-screen content of the display based on the angle.

In one aspect, a non-transitory computer readable medium comprises computer executable instructions which when executed by a computer cause the computer to perform the method of: determining a comfortability-tension threshold for a user; comparing a current pose of the user and a determined optimal pose; mapping the current pose and the determined optimal pose to an angle for adjusting on-screen content of a display of the computer system; and adjusting the on-screen content of the display of the computer system based on the angle.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments provide one or more of:

training of an individual's lazy eye without the need for extra sensors or devices;

no special task for the user to perform while training;

intelligent tracking of an actor's pose that factors in the suitability of on-screen content and noise;

modeling the relationship between physiological variables and a corrective pose to train the lazy eye;

using an autoregressive neural network model to predict at least one factor for which a balance exists between being comfortable reading content and training the lazy eye; and an adjustment of on-screen content that intelligently considers the comfort and convenience of the user, prompts the user to adjust the user's pose to train a lazy eye, and further reinforces proper ergonomic behavior.

These and other features and advantages of the present invention will become apparent from the following detailed description of illustrative embodiments thereof, which is to be read in connection with the accompanying drawings.

DETAILED DESCRIPTION

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
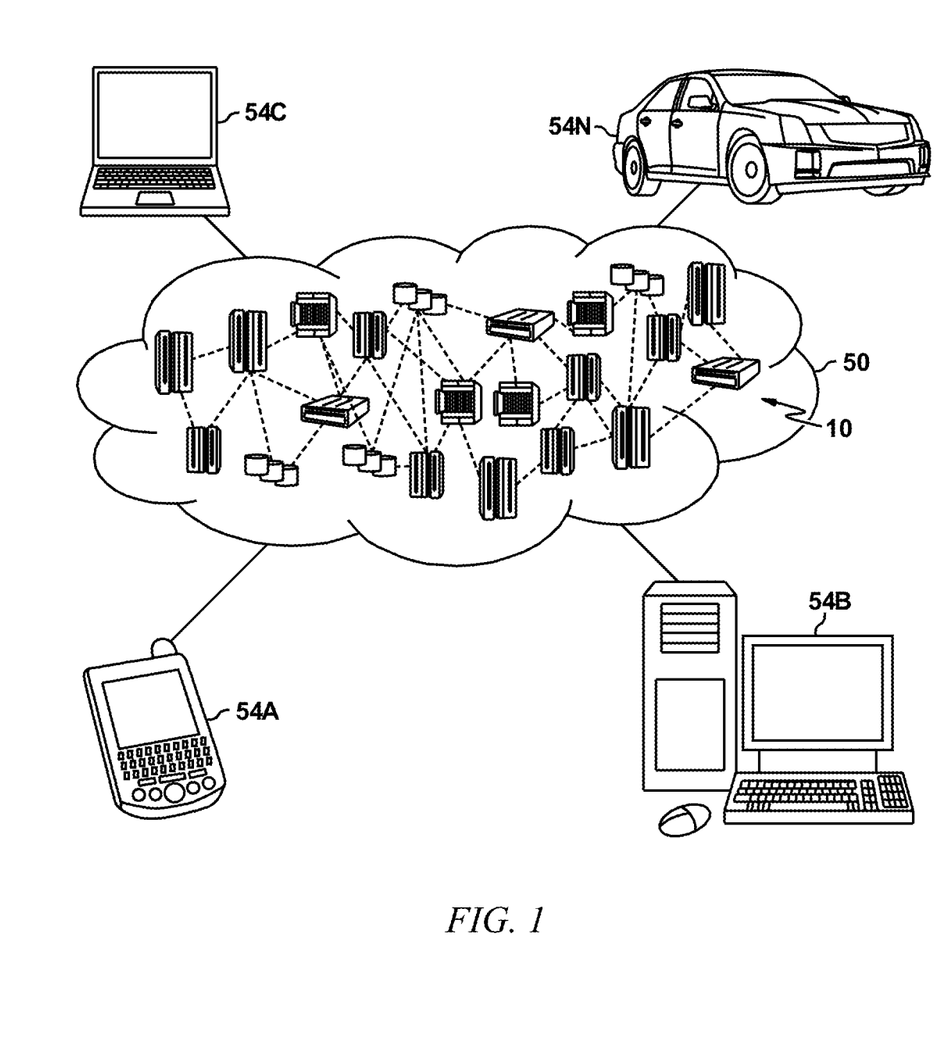
FIG. 1 depicts a cloud computing environment according to an embodiment of the present invention.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
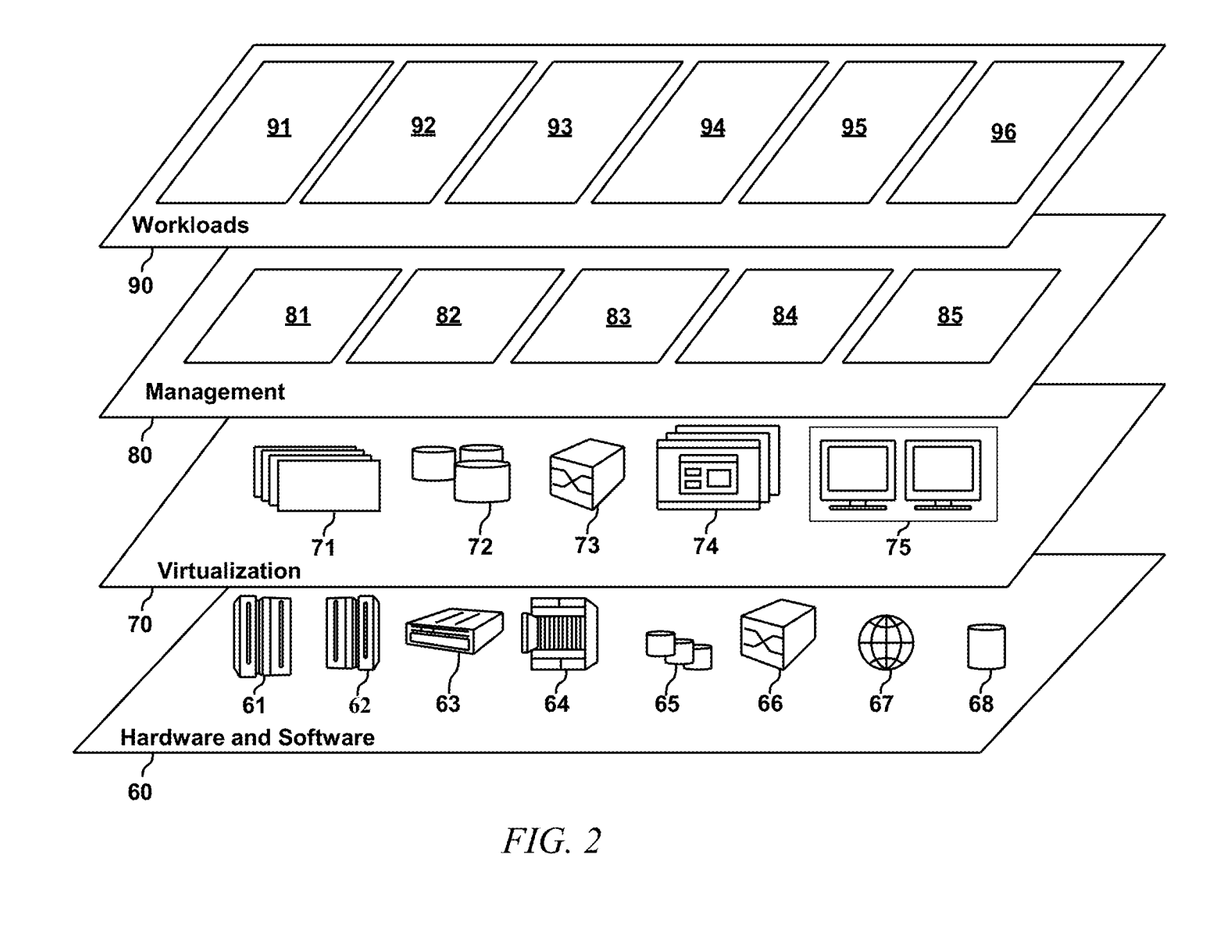
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and lazy eye trainer 96. It should be noted that cloud, non-cloud, and partial cloud implementations of one or more embodiments are contemplated.

Generally, systems and methods that reactively and intelligently adjust the angle of content on a screen of a computer (such as a PC, smart phone, tablet computer, and the like) to train a lazy eye of an individual are disclosed. People with particularly severe amblyopia tend to subconsciously adjust the angle of their heads slightly to better focus with the stronger eye while using a computer. This behavior further suppresses use of the lazy eye and leads to less binocular acuity. In one example embodiment, the front facing camera of a computer is leveraged to detect and mitigate this behavior while ensuring that the user (user and actor are used interchangeably herein) is able to comfortably read the contents displayed on the screen.

In a first example embodiment, the system intelligently tracks the position and angle of the head of the user and the iris of the lazy eye. The tracking may be based on the suitability of the current content of the screen to serve as a training example. For example, video is less suitable and text is more suitable for lazy eye training as the viewing angle of text is easier to adjust than the viewing angle of video. If the system detects an appropriate position and angle of the head and iris, the angle of the content on the screen is maintained. If the system detects an inappropriate position or angle of either the head or iris, the angle of the content on the screen is adjusted in a three-dimensional perspective, such as by modifying a document object model (DOM) of content on a web-browser in three dimensions.

In one example embodiment, the adjustment is based on a comfortability-tension threshold, as described more fully below. The adjustment prompts the user to adjust the user's overall pose, moving the position and/or angle of the head and/or iris to an appropriate position/angle for training the lazy eye. The comfortability-tension threshold (CT-threshold) ensures that the adjustment maintains an acceptable comfort level for the user.

In a second example embodiment, given the position and/or angle of the head and/or iris, the system computes an adjustment angle of the content based on the training history of the user and the comfortability-tension threshold. The system updates the training history of the user and optionally adjusts the comfortability-tension threshold based on the training history, if necessary. In one example embodiment, the comfortability-tension threshold is a vector based on the training history (for example, the training history is used to infer the CT-threshold). The comfortability-tension threshold (and training history) can be stored, for example, in a local data store and may be updated by protocols supported by the local data store.

In a third example embodiment, given training history data from multiple amblyopic users, the system generates a global model of the relationships between various predictor variables (such as user age, gender, degrees of amblyopia (such as the degree of different head tilting angles), and the like) and the comfortability-tension threshold(s). The system then intelligently adjusts the angle of the content on the screen based on the characteristics of a given user and the global model.

Figure 3:
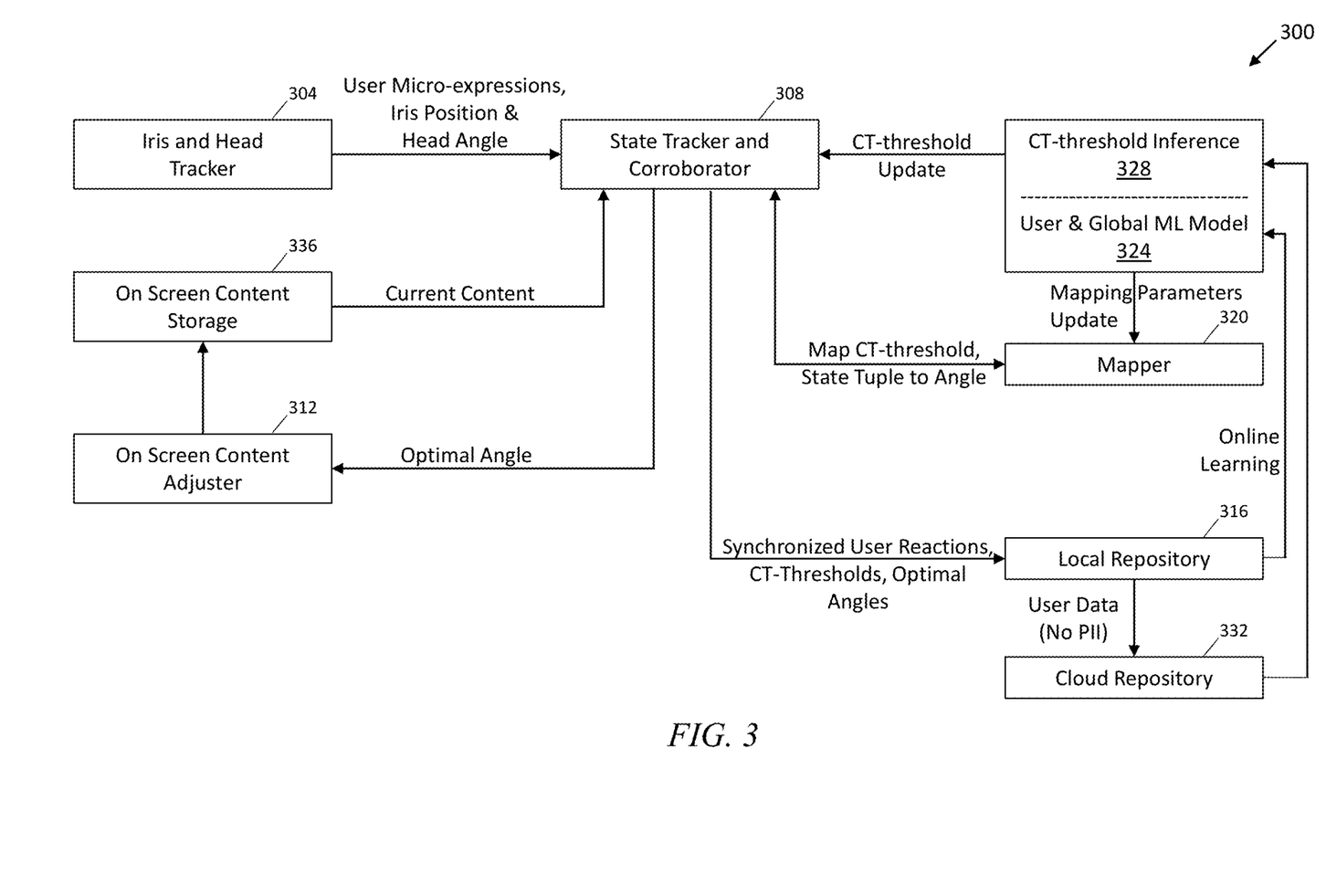
FIG. 3 is a block diagram of an example system for training a lazy eye, in accordance with an example embodiment.

Reference should now be had to FIG. 3, which is a block diagram of an example system 300 for training a lazy eye, in accordance with an example embodiment. The exemplary system 300 includes an iris and head tracker 304, on-screen content storage 336, a state tracker and corroborator 308, an on-screen content adjuster 312, a local repository 316, a mapper 320, a user and global machine learning (ML) model 324, CT-threshold inference 328, and a cloud repository 332. Non-cloud repositories in lieu of or in addition to the cloud repository 332 are also possible. In addition, the local repository 316, the mapper 320, the user and global machine learning (ML) model 324, and the CT-threshold inference 328 may be cloud-based.

The iris and head tracker 304 utilizes captured images of a user to track the position and angle of the user's head and iris. A variety of algorithms are available for implementing head and iris tracking. (See, for example, George, Anjith & Routray, Aurobinda. (2016). A Fast and Accurate Algorithm for Eye Localization for Gaze Tracking in Low Resolution Images. IET Computer Vision. 10. 10.1049/iet-cvi.2015.0316.)

The state tracker and corroborator 308 maintains the current state of the user (including the user's micro-expressions (ME), and head and pupil positions as determined using a set of markers) and generates a state history for the user for a plurality of time steps. The state history also includes the content adjustment angle (also referred to as the applied angle or angle herein) for each time step. The position and angle of the actor's head and pupil(s) are also corroborated with the optimal pose of the user based on the on-screen content and the CT-threshold, as described more fully below.

The on-screen content adjuster 312 adjusts the viewing angle of the content. Tools for adjusting the viewing angle of content are generally available. For example, known commercially available developer tools provide for the rotation and re-orientation of a three-dimensional presentation of a web page. The adjusted content is stored in on-screen content storage 336. The local repository 316 stores, for example, time-step synchronized user-reactions (such as user micro-expressions), system state (such as the head and pupil position using the set markers), the computed optimal angle for the content, and the CT-threshold(s) for a single user.

The mapper 320 maps the current pose (current state) of the user and the CT-threshold to a viewing angle for the content. In one example embodiment, as described more fully below, the optimal pose is computed by calculating a dot product of the CT-threshold and the system state and the content angle is computed by calculating a rotation matrix for which the current pose is rotated to attain the optimal pose.

The user and global ML model 324 generates and stores the relationships between various predictor variables (such as user age, gender, degrees of amblyopia (such as the degree of different head tilting angles), and the like) and the comfortability-tension threshold(s).

The CT-threshold inference 328 computes new CT-threshold vectors based on user history, previous CT-thresholds, and the synchronized user reactions. The cloud repository 332 stores, for example, time-step synchronized user-reactions (such as micro-expressions (ME)), system state (such as the head and pupil position using the set markers), the computed optimal angle for the content, and CT-thresholds for multiple users.

Figure 4:
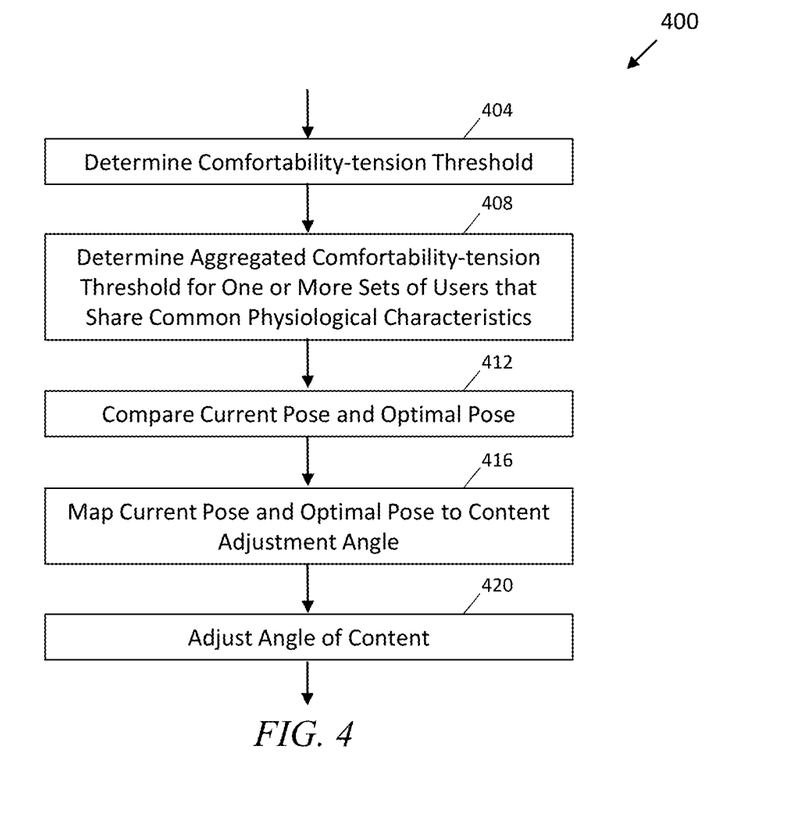
FIG. 4 is a flowchart for an example method for training a lazy eye, in accordance with an example embodiment.

FIG. 4 is a flowchart for an example method 400 for training a lazy eye, in accordance with an example embodiment. The method 400 provides for the conditional tracking of the pupil and head of the actor (the pose) while the actor is facing a screen. In general, as described above, not all content on the screen is suitable to trigger tracking. In addition, tracking is contingent on, for example, a specified training goal for the day, such as a number of hours allotted to train the eye. The suitability of content to serve as a training example is determined by a suitability score, as described more fully below.

In one example embodiment, a comfortability-tension threshold for an individual user is determined (operation 404). The comfortability-tension threshold parameterizes the optimal pose (of a user) that balances a comfort level of the user interacting with the content with the effectiveness of training the lazy eye. The comfortability-tension threshold provides a limit on any discomfort suffered by a user. An aggregated comfortability-tension threshold for a set(s) of a plurality of users is determined where each set of users shares common physiological characteristics (operation 408). Common physiological characteristics include user age, degree of amblyopia, position of the set markers on the head/pupil, physical size, and the like. While the system may operate without computing an aggregated comfortability-tension threshold, it may prove useful as a default comfortability-tension threshold for the first time a user interacts with the system 300. The current pose of a given actor is compared with the determined optimal pose (operation 412). In one example embodiment, the pose points include the pupil rotation angle, the angle of prominent facial areas (such as eyebrows, eye corners, mouth corners, and chin), and the like. The current pose and the determined optimal pose are mapped to an angle for which the on-screen content should be adjusted (operation 416). As noted above, the content angle may be computed by calculating a rotation matrix for which the current pose is rotated to attain the optimal pose. The content is then rotated, if necessary, to match the computed angle (operation 420).

Figure 5:
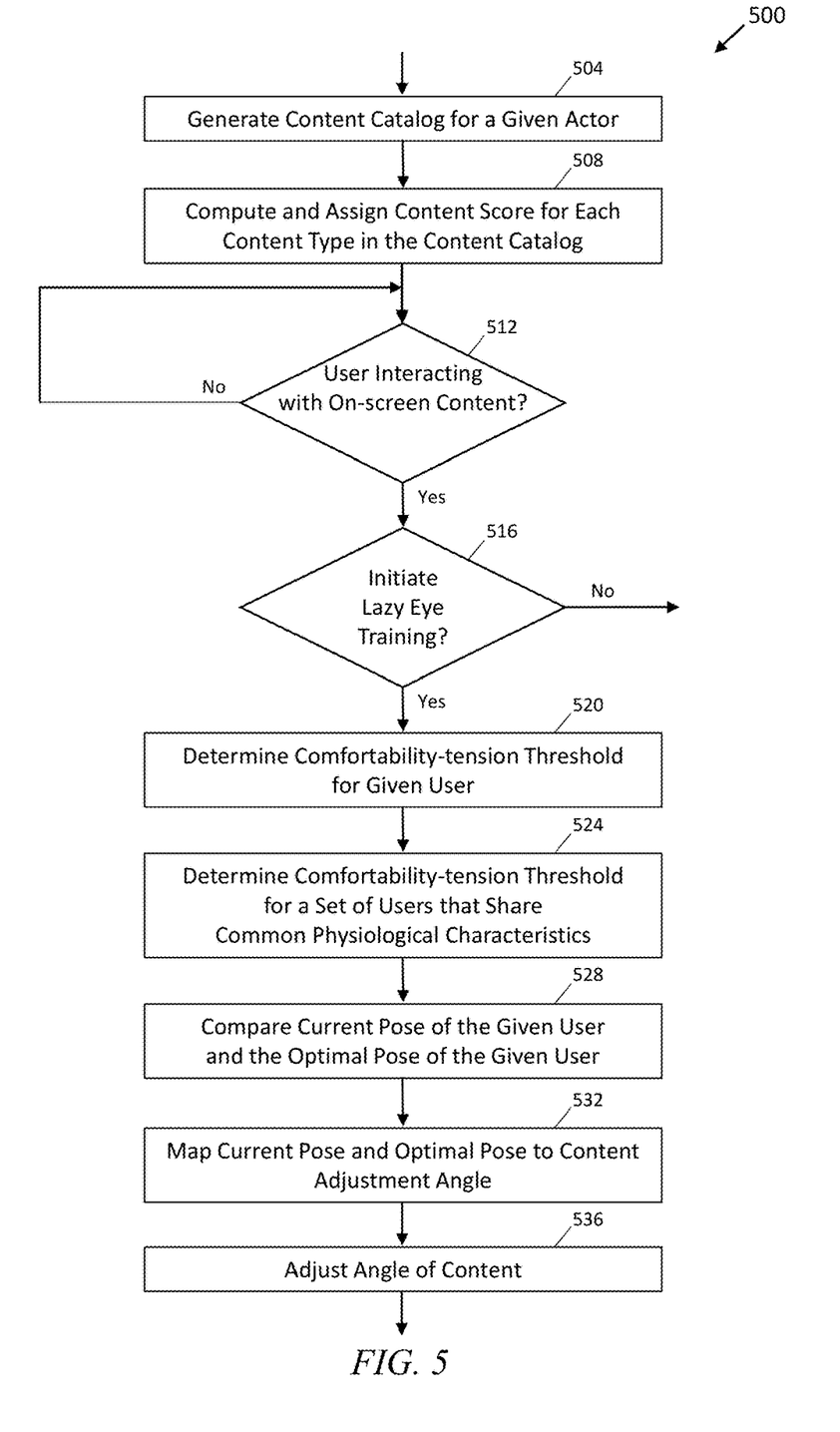
FIG. 5 is a flowchart for a second example method for training a lazy eye, in accordance with an example embodiment.

FIG. 5 is a flowchart for a second example method 500 for training a lazy eye, in accordance with an example embodiment. The method 500 provides for intelligent and conditional tracking of the actor's pupil(s) and head, and factors in the suitability of on-screen content, noise, and a training goal. (Noise, as used herein, refers to scenarios where on-screen content and pose pair is considered as a training example when it should not be, such as when the user suddenly moves their head due to stimuli external to the system 300.) In one example embodiment, the content that the actor interacts with, such as a code editor, a website, and the like, is cataloged (operation 504). A suitability score is computed and assigned for each content type in the content catalog (operation 508). In one example embodiment, the suitability score is an adaptive measure that is updated based on various variables. In one example embodiment, the variables are the historical time a user interacts with the content (which may be retrieved from the operating system program manager); the category of the content (video, text, coding, software (such as text processing)), and the like; and the historical number of times the system 300 has had to make a corrective recommendation (i.e., adjust the content to trigger an optimal pose). A linear function of this variable may then be used to compute the suitability score. In one example embodiment, a singular value decomposition based algorithm is used. In this embodiment, the goal is to identify k clusters and then have a human expert assign scores to each cluster. When a new data point (such as a new content type) is to be evaluated, the score corresponding to the cluster to which the data point belongs is selected as the suitability score.

The suitability may consider the type of content, the amount of time a user interacts with the content, and the like. In response to a user interacting with on-screen content (YES branch of decision block 512), a determination is made of whether to initiate lazy eye training (operation 516); otherwise (NO branch of decision block 512), the method 500 repeats operation 512.

In one example embodiment, training is only initiated if a training goal, such as a daily training goal based on an amount of time allotted for training, has not been attained. If the daily training goal has been met and training is not to be initiated (NO branch of decision block 516), the method 500 ends. If the daily training goal has not been met and training is to be initiated (YES branch of decision block 516), a comfortability-tension threshold for an individual user is determined (operation 520) and an aggregated comfortability-tension threshold for a set(s) of a plurality of users is determined where each set of users shares common physiological characteristics (operation 524). The current pose of a given actor is compared with the determined optimal pose (operation 528). The current pose and the determined optimal pose are mapped to an angle for which the on-screen content should be adjusted (operation 532). The content is then rotated, if necessary, to match the computed angle (operation 536).

Figure 6:
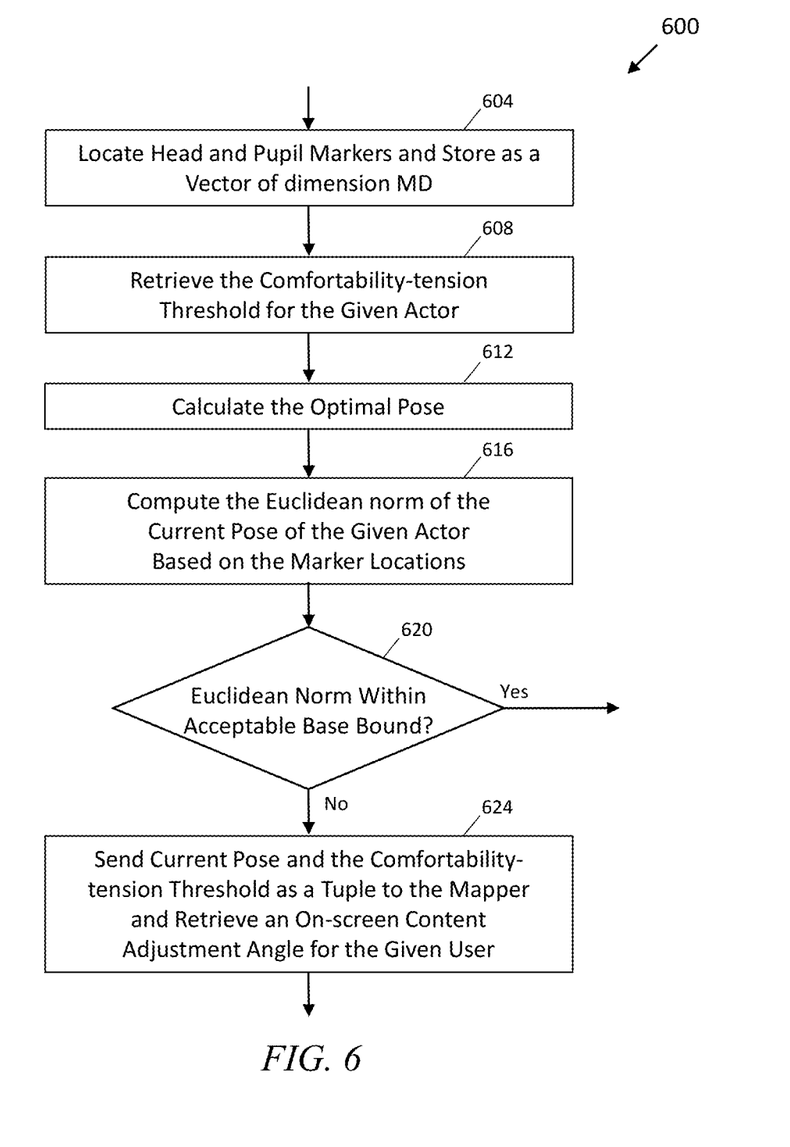
FIG. 6 is a flowchart for an example method for corroborating the pose of a given actor, in accordance with an example embodiment.

FIG. 6 is a flowchart for an example method 600 for corroborating the pose of a given actor, in accordance with an example embodiment. The method 600 provides for corroborating the position and angle of the actor's head and pupil(s) with the optimal pose based on the on-screen content and the CT-threshold. In one example embodiment, markers corresponding to the head and pupil(s) of the user are located and stored as a vector of dimension MD (operation 604). The CT-threshold for a given actor is retrieved (operation 608). The optimal pose is calculated (operation 612) and the Euclidean distance between the current pose and the optimal pose is calculated based on the location of the markers (operation 616). In one example embodiment, the optimal pose is calculated by scaling the baseline pose (the pose that is exactly perpendicular to the on-screen content) with the CT-threshold. In this case, a dot product may be used. If the Euclidean distance of the current pose is within an acceptable base bound (YES branch of decision block 620), then no further action is taken. (In one example embodiment, since the base bound gives the minimal acceptable distance that a user's pose can be from the optimal pose, it is initialized to a small number drawn randomly from a uniform distribution with a mean, for example, of 24 mm and a standard deviation of 1.) Otherwise, if the Euclidean distance of the current pose is not within an accepted base bound (NO branch of decision block 620), the current pose and CT-threshold is sent as a tuple to the mapper 320 and a new angle for which to adjust the on-screen content is obtained (operation 624).

Figure 7:
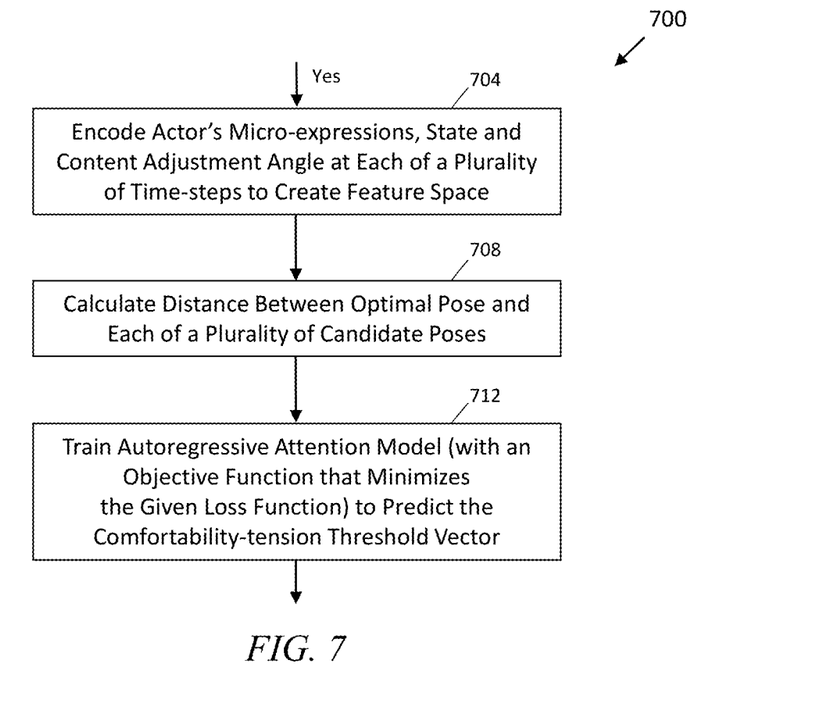
FIG. 7 is a flowchart for an example method for determining a model that infers the comfortability-tension (CT) threshold for a specific actor using variables, in accordance with an example embodiment.

FIG. 7 is a flowchart for an example method 700 for determining a model that infers the CT-threshold for a specific actor (the actor model) using variables, in accordance with an example embodiment. The variables include the historical synchronized actor micro-expressions (for on-screen content adjustments), physiological characteristics of the actor including the degree of amblyopia, and the like. In one example embodiment, the actor's micro-expression(s), system state (including the head and pupil positions as determined using the set markers), and content adjustment angle (the angle applied to the content) are encoded into a vector for each of a plurality of time steps to create a feature space (operation 704). In other words, the cited parameters are measured over a series of time steps. In one example embodiment, the micro-expressions captured are based on defined micro-expressions (See, for example, Pfister, Tomas et al. "Recognising spontaneous facial micro-expressions." 2011 *International Conference on Computer Vision* (2011): 1449-1456 for a discussion of micro-expressions.). In one example embodiment, the final vector has a dimension of 12: [$ME_1, \ldots, ME_{10}, PC, HPS_1, \ldots, HPS_{10}, CA$] where $ME_1, \ldots, ME_{10}$ is a micro-expression variable with a dimension of 10 (corresponding to 10 pose points/markers on the face); PC are the physiological characteristics (such as degree of amblyopia); $HPS_1, \ldots, HPS_{10}$ are the head and pupil position (such as the positions identified by 10 markers): and CA is the content adjustment angle.

In one example embodiment, the Euclidean distance between different candidate poses and what is predicted to be comfortable for the user (the optimal pose) is calculated (operation 708). An autoregressive attention model is trained to predict the CT-threshold vector with an objective function that minimizes the loss function, as described more fully below (operation 712), where each physical alignment has a corresponding score that indicates how comfortable the pose is based on the micro-expression(s) of the user.

In one example embodiment, given a distribution of alignments DA (as defined by the system state and the angle of content), each alignment is scored based on the user's micro-expression at the corresponding time step. A distance metric of the predicted pose (CT-threshold*baseline pose) and the distribution of alignments DA is computed. The calculated value becomes the loss to minimize using an optimizer, such as a stochastic gradient descent.

In one example embodiment, the method 700 provides for determining a model that infers the CT-threshold for multiple actors based on a global model where the multiple actors share similar physiological characteristics. The model is then leveraged as a basis for the actor model for a given actor. As described above, the actor model is trained on data from single actors where each actor's micro-expression (ME), system state, and content adjustment at each time step are stored as vectors to form the feature space. The global model is trained on data from multiple actors using additional features characterizing the physiology of the actor, such as the actor's age, degree of amblyopia, and positions of set markers on the head and pupil.

Figure 8:
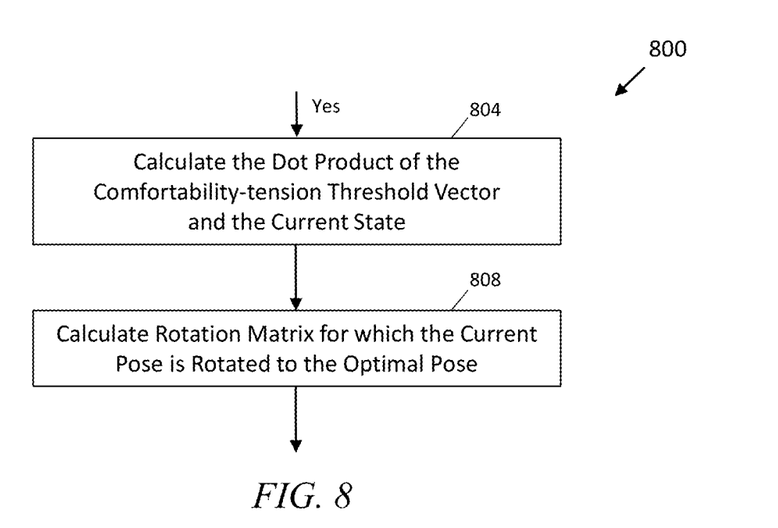
FIG. 8 is a flowchart for a fourth example method 800 for generating a mapping function, in accordance with an example embodiment.

FIG. 8 is a flowchart for an example method 800 for generating a mapping function, in accordance with an example embodiment. The method 800 provides for mapping the tuple of the CT-threshold and the current system state (such as the current head angle, pupil position, and micro expressions) to an optimal angle for which the on-screen content should be adjusted. In one example embodiment, the optimal pose is calculated by calculating the dot product of the CT-threshold and the current state (operation 804), and a rotation matrix is calculated for which the current pose is rotated to the optimal pose (operation 808).

Given the discussion thus far, it will be appreciated that, in general terms, an exemplary method, according to an aspect of the invention, includes the operations of determining a comfortability-tension threshold for a user (operation 404); comparing a current pose of the user and a determined optimal pose (operation 412); mapping the current pose and the determined optimal pose to an angle for adjusting on-screen content of a display of the computer system (operation 416); and adjusting the on-screen content of the display of the computer system based on the angle (operation 420).

In one example embodiment, the comfortability-tension threshold parameterizes the optimal pose, the optimal pose balancing a comfort level of the user interacting with the on-screen content and an effectiveness of the training of the lazy eye. In one example embodiment, an aggregated comfortability-tension threshold is determined for a set of a plurality of users who share one or more common physiological characteristics, wherein the optimal pose is based on the aggregated comfortability-tension threshold. In one example embodiment, a dot product of the comfortability-tension threshold and a system state is calculated to compute the determined optimal pose. In one example embodiment, a subject with a lazy eye is trained using the adjusted on-screen content.

In one example embodiment, a rotation matrix for which the current pose is rotated to the optimal pose is calculated to compute the angle. In one example embodiment, a system state for a time step comprises one or more micro-expressions of the user, head and pupil positions as determined using a set of markers, and the determined angle.

In one example embodiment, a position and angle of a head and at least one pupil of the user is corroborated with the optimal pose based on the on-screen content and the comfortability-tension threshold by: locating one or more markers corresponding to the head and at least one pupil of the user (operation 604); retrieving the comfortability-tension threshold for the user (operation 608); calculating the optimal pose (operation 612); calculating a Euclidean distance between the current pose and the optimal pose based on the location of the markers (operation 616); maintaining the angle in response to the Euclidean distance being within an acceptable base bound; and wherein the adjusting operation is performed in response to the Euclidean distance not being within the acceptable base bound.

In one example embodiment, the optimal pose is calculated by scaling a baseline pose with the comfortability-tension threshold, the baseline pose being perpendicular to the on-screen content.

In one example embodiment, a model that infers the comfortability-tension threshold for the user is determined using variables, the variables comprising one or more historical synchronized actor micro-expressions and one or more physiological characteristics of the actor, by: encoding the one or more historical synchronized actor micro-expressions, a system state, and a content adjustment angle into a vector at each of a plurality of time steps to create a feature space (operation 704); calculating a distance between the optimal pose and each of one or more candidate poses (operation 708); and training the model to predict a comfortability-tension threshold vector with an objective function that minimizes a loss function, wherein each alignment of a distribution of alignments has a corresponding score based on the one or more historical synchronized actor micro-expressions at the corresponding time step, each alignment being defined by the corresponding system state and the corresponding content adjustment angle (operation 712).

In one aspect, an apparatus comprises a memory; a display; and at least one processor, coupled to said memory and said display, and operative to perform operations comprising determining a comfortability-tension threshold for a user (operation 404); comparing a current pose of the user and a determined optimal pose (operation 412); mapping the current pose and the determined optimal pose to an angle for adjusting on-screen content of the display (operation 416); and adjusting the on-screen content of the display based on the angle (operation 420).

In one aspect, a non-transitory computer readable medium comprises computer executable instructions which when executed by a computer cause the computer to perform the method of: determining a comfortability-tension threshold for a user (operation 404); comparing a current pose of the user and a determined optimal pose (operation 412); mapping the current pose and the determined optimal pose to an angle for adjusting on-screen content of a display of the computer system (operation 416); and adjusting the on-screen content of the display of the computer system based on the angle (operation 420).

Figure 9:
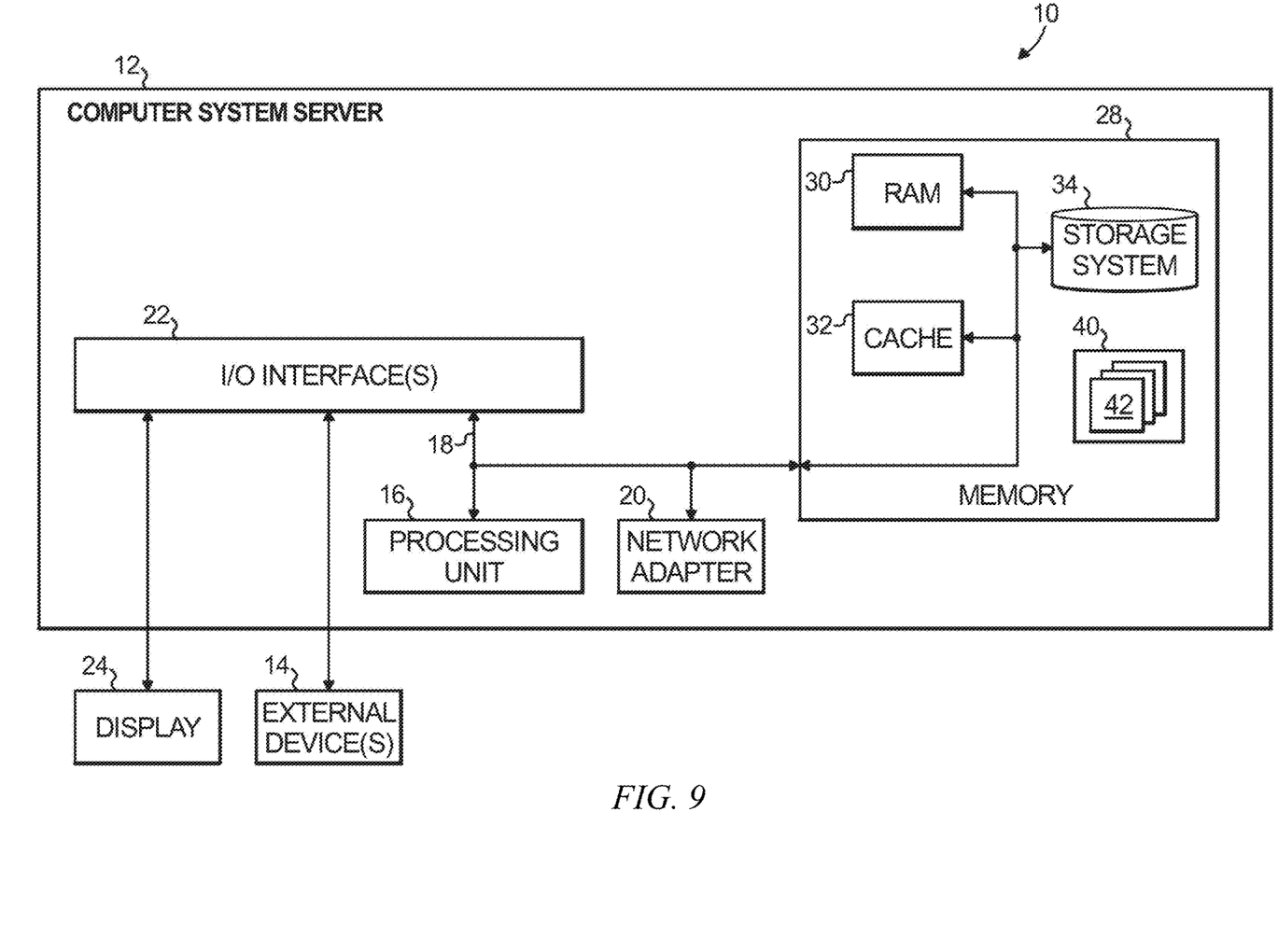
FIG. 9 depicts a computer system that may be useful in implementing one or more aspects and/or elements of the invention, also representative of a cloud computing node according to an embodiment of the present invention.

One or more embodiments of the invention, or elements thereof, can be implemented in the form of an apparatus including a memory and at least one processor that is coupled to the memory and operative to perform exemplary method steps. FIG. 9 depicts a computer system that may be useful in implementing one or more aspects and/or elements of the invention, also representative of a cloud computing node according to an embodiment of the present invention. Referring now to FIG. 9, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 9, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12;

and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 9, such an implementation might employ, for example, a processor 16, a memory 28, and an input/output interface 22 to a display 24 and external device(s) 14 such as a keyboard, a pointing device, a camera, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 9) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for training a lazy eye with a computer system, the method comprising:
   determining a comfortability-tension threshold for a user;
   comparing a current pose of the user and a determined optimal pose;
   mapping the current pose and the determined optimal pose to an angle for adjusting on-screen content of a display of the computer system; and
   adjusting the on-screen content of the display of the computer system based on the angle.

2. The method of claim 1, wherein the comfortability-tension threshold parameterizes the optimal pose, the optimal pose balancing a comfort level of the user interacting with the on-screen content and an effectiveness of the training of the lazy eye.

3. The method of claim 1, further comprising determining an aggregated comfortability-tension threshold for a set of a plurality of users who share one or more common physiological characteristics and wherein the optimal pose is based on the aggregated comfortability-tension threshold.

4. The method of claim 1, further comprising calculating a dot product of the comfortability-tension threshold and a system state to compute the determined optimal pose.

5. The method of claim 1, further comprising training a subject with a lazy eye using the adjusted on-screen content of the display of the computer system.

6. The method of claim 1, further comprising calculating a rotation matrix for which the current pose is rotated to the optimal pose to compute the angle.

7. The method of claim 1, wherein a system state for a time step comprises one or more micro-expressions of the user, head and pupil positions as determined using a set of markers, and the determined angle.

8. The method of claim 1, further comprising corroborating a position and angle of a head and at least one pupil of the user with the optimal pose based on the on-screen content and the comfortability-tension threshold by:
locating one or more markers corresponding to the head and at least one pupil of the user;
retrieving the comfortability-tension threshold for the user;
calculating the optimal pose;
calculating a Euclidean distance between the current pose and the optimal pose based on the location of the markers;
maintaining the angle in response to the Euclidean distance being within an acceptable base bound; and
wherein the adjusting operation is performed in response to the Euclidean distance not being within the acceptable base bound.

9. The method of claim 8, wherein the optimal pose is calculated by scaling a baseline pose with the comfortability-tension threshold, the baseline pose being perpendicular to the on-screen content.

10. The method of claim 1, further comprising determining a model that infers the comfortability-tension threshold for the user using variables, the variables comprising one or more historical synchronized actor micro-expressions and one or more physiological characteristics of the actor, by:
encoding the one or more historical synchronized actor micro-expressions, a system state, and a content adjustment angle into a vector at each of a plurality of time steps to create a feature space;
calculating a distance between the optimal pose and each of one or more candidate poses; and
training the model to predict a comfortability-tension threshold vector with an objective function that minimizes a loss function, wherein each alignment of a distribution of alignments has a corresponding score based on the one or more historical synchronized actor micro-expressions at the corresponding time step, each alignment being defined by the corresponding system state and the corresponding content adjustment angle.

11. A non-transitory computer readable medium comprising computer executable instructions which when executed by a computer cause the computer to perform the method of:
determining a comfortability-tension threshold for a user;
comparing a current pose of the user and a determined optimal pose;
mapping the current pose and the determined optimal pose to an angle for adjusting on-screen content of a display of the computer; and
adjusting the on-screen content of the display of the computer based on the angle.

12. The non-transitory computer readable medium of claim 11, the method further comprising corroborating a position and angle of a head and at least one pupil of the user with the optimal pose based on the on-screen content and the comfortability-tension threshold by:
locating one or more markers corresponding to the head and at least one pupil of the user;
retrieving the comfortability-tension threshold for the user;
calculating the optimal pose;
calculating a Euclidean distance between the current pose and the optimal pose based on the location of the markers;
maintaining the angle in response to the Euclidean distance being within an acceptable base bound; and
wherein the adjusting operation is performed in response to the Euclidean distance not being within the acceptable base bound.

13. An apparatus comprising:
a memory;
a display; and
at least one processor, coupled to said memory and said display, and operative to perform operations comprising:
determining a comfortability-tension threshold for a user;
comparing a current pose of the user and a determined optimal pose;
mapping the current pose and the determined optimal pose to an angle for adjusting on-screen content of the display; and
adjusting the on-screen content of the display based on the angle.

14. The apparatus of claim 13, wherein the comfortability-tension threshold parameterizes the optimal pose, the optimal pose balancing a comfort level of the user interacting with the on-screen content and an effectiveness of the training of the lazy eye.

15. The apparatus of claim 13, the operations further comprising determining an aggregated comfortability-tension threshold for a set of a plurality of users who share one or more common physiological characteristics and wherein the optimal pose is based on the aggregated comfortability-tension threshold.

16. The apparatus of claim 13, the operations further comprising calculating a dot product of the comfortability-tension threshold and a system state to compute the determined optimum pose and calculating a rotation matrix for which the current pose is rotated to the optimal pose to compute the angle.

17. The apparatus of claim 13, wherein a system state for a time step comprises one or more micro-expressions of the user, head and pupil positions as determined using a set of markers, and the determined angle.

18. The apparatus of claim 13, the operations further comprising corroborating a position and angle of a head and at least one pupil of the user with the optimal pose based on the on-screen content and the comfortability-tension threshold by:
locating one or more markers corresponding to the head and at least one pupil of the user;

retrieving the comfortability-tension threshold for the user;

calculating the optimal pose;

calculating a Euclidean distance between the current pose and the optimal pose based on the location of the markers;

maintaining the angle in response to the Euclidean distance being within an acceptable base bound; and wherein the adjusting operation is performed in response to the Euclidean distance not being within the acceptable base bound.

19. The apparatus of claim 18, wherein the optimal pose is calculated by scaling a baseline pose with the comfortability-tension threshold, the baseline pose being perpendicular to the on-screen content.

20. The apparatus of claim 13, the operations further comprising determining a model that infers the comfortability-tension threshold for the user using variables, the variables comprising one or more historical synchronized actor micro-expressions and one or more physiological characteristics of the actor, by:

encoding the one or more historical synchronized actor micro-expressions, a system state, and a content adjustment angle into a vector at each of a plurality of time steps to create a feature space;

calculating a distance between the optimal pose and each of one or more candidate poses; and training the model to predict a comfortability-tension threshold vector with an objective function that minimizes a loss function, wherein each alignment of a distribution of alignments has a corresponding score based on the one or more historical synchronized actor micro-expressions at the corresponding time step, each alignment being defined by the corresponding system state and the corresponding content adjustment angle.

* * * * *